(12) United States Patent
Chang et al.

(10) Patent No.: US 10,272,541 B2
(45) Date of Patent: *Apr. 30, 2019

(54) POLISHING LAYER ANALYZER AND METHOD

(71) Applicants: Rohm and Haas Electronic Materials CMP Holdings, Inc., Newark, DE (US); Dow Global Technologies LLC, Midland, MI (US)

(72) Inventors: Scott Chang, Taipei (TW); Jeff Tsai, Chunan (TW); Francis V. Acholla, New Castle, DE (US); Andrew Wank, Avondale, PA (US); Mark Gazze, Lincoln University, PA (US); William A. Heeschen, Midland, MI (US); James David Tate, Lake Jackson, TX (US); Leo H. Chiang, Pearland, TX (US); Swee-Teng Chin, Pearland, TX (US)

(73) Assignees: Rohm and Haas Electronic Matericals CMP Holdings, Inc., Newark, DE (US); Dow Global Technologies LLC, Midland, MI (US)

( * ) Notice: Subject to any disclaimer, the term of this patent is extended or adjusted under 35 U.S.C. 154(b) by 193 days.

This patent is subject to a terminal disclaimer.

(21) Appl. No.: 15/004,270

(22) Filed: Jan. 22, 2016

(65) Prior Publication Data
US 2017/0209979 A1    Jul. 27, 2017

(51) Int. Cl.
| B24B 49/12 | (2006.01) |
| G01N 21/958 | (2006.01) |
| G01N 21/59 | (2006.01) |
| B24B 37/26 | (2012.01) |
| B24B 37/34 | (2012.01) |
| B24B 1/00 | (2006.01) |
| H01L 21/321 | (2006.01) |
| B24B 37/20 | (2012.01) |
| H01L 21/768 | (2006.01) |

(52) U.S. Cl.
CPC .............. *B24B 49/12* (2013.01); *B24B 37/26* (2013.01); *B24B 37/34* (2013.01); *G01N 21/59* (2013.01); *G01N 21/958* (2013.01); *B24B 1/00* (2013.01); *B24B 37/20* (2013.01); *H01L 21/3212* (2013.01); *H01L 21/7684* (2013.01)

(58) Field of Classification Search
None
See application file for complete search history.

(56) References Cited

U.S. PATENT DOCUMENTS

| 627,821 | A | 6/1899 | Gurnee |
| 2,957,269 | A | 2/1959 | Nohl et al. |
| 3,906,647 | A | 9/1975 | Bates, Jr. |
| 4,526,445 | A | 7/1985 | Wogoman |
| 5,358,123 | A | 10/1994 | Stone |
| 5,708,506 | A | 1/1998 | Birang |
| 5,961,369 | A | 10/1999 | Bartels et al. |
| 6,164,633 | A | 12/2000 | Mulligan et al. |
| 6,538,733 | B2 | 3/2003 | Gaal et al. |

(Continued)

*Primary Examiner* — Sylvia MacArthur
(74) *Attorney, Agent, or Firm* — Thomas S. Deibert; Andrew Merriam; Blake T. Biederman (57) ABSTRACT

A polishing layer analyzer is provided, wherein the analyzer is configured to detect macro inhomogeneities is polymeric sheets and to classify the polymeric sheets as either acceptable or suspect.

5 Claims, 7 Drawing Sheets

(56) References Cited

U.S. PATENT DOCUMENTS

| | | |
|---|---|---|
| 6,650,408 B2 | 11/2003 | Jun et al. |
| 7,027,640 B2 | 4/2006 | Park et al. |
| 7,207,862 B2 | 4/2007 | Nabeya et al. |
| 7,241,201 B2 | 7/2007 | Eischeid et al. |
| 8,011,999 B2 | 9/2011 | Nagase et al. |
| 9,737,971 B2* | 8/2017 | Acholla ................ B24B 37/013 |
| 2017/0209979 A1* | 7/2017 | Chang .................... B24B 49/12 |

* cited by examiner

POLISHING LAYER ANALYZER AND METHOD

This application claims priority to U.S. Provisional Application No. 62/110,059 filed on Jan. 30, 2015.

The present invention relates generally to the field of manufacture of chemical mechanical polishing pads. In particular, the present invention is directed to a polishing layer analyzer and related methods.

In the fabrication of integrated circuits and other electronic devices, multiple layers of conducting, semiconducting and dielectric materials are deposited on or removed from a surface of a semiconductor wafer. Thin layers of conducting, semiconducting, and dielectric materials may be deposited by a number of deposition techniques. Common deposition techniques in modem processing include physical vapor deposition (PVD), also known as sputtering, chemical vapor deposition (CVD), plasma-enhanced chemical vapor deposition (PECVD), and electrochemical plating (ECP).

As layers of materials are sequentially deposited and removed, the uppermost surface of the wafer becomes non-planar. Because subsequent semiconductor processing (e.g., metallization) requires the wafer to have a flat surface, the wafer needs to be planarized. Planarization is useful in removing undesired surface topography and surface defects, such as rough surfaces, agglomerated materials, crystal lattice damage, scratches, and contaminated layers or materials.

Chemical mechanical planarization, or chemical mechanical polishing (CMP), is a common technique used to planarize substrates, such as semiconductor wafers. In conventional CMP, a wafer is mounted on a carrier assembly and positioned in contact with a polishing pad in a CMP apparatus. The carrier assembly provides a controllable pressure to the wafer, pressing it against the polishing pad. The pad is moved (e.g., rotated) relative to the wafer by an external driving force. Simultaneously therewith, a chemical composition ("slurry") or other polishing solution is provided between the wafer and the polishing pad. Thus, the wafer surface is polished and made planar by the chemical and mechanical action of the pad surface and slurry.

In U.S. Pat. No. 5,578,362, Reinhardt et al. disclose an exemplary polishing pad known in the art. The polishing pad of Reinhardt comprises a polymeric matrix having microspheres dispersed throughout. Generally, the microspheres are blended and mixed with a liquid polymeric material and transferred to a mold for curing. The molded article is then sliced to form polishing layers. Unfortunately, polishing layers formed in this manner may exhibit unwanted defects that may, when incorporated into a polishing pad, cause defects to a substrate polished therewith.

One asserted approach for addressing the concern regarding potential defects in the polishing layers of chemical mechanical polishing pads is disclosed by Park et al. in U.S. Pat. No. 7,027,640. Park et al. disclose an apparatus for detecting or inspecting defects on a pad for use in performing chemical mechanical polishing of a wafer, comprising: a pad driving device for loading the pad thereon and moving the pad; a camera installed to face the pad for converting an image of the pad into an electrical signal and outputting the converted electrical signal; a digital image data acquisition device for converting the electrical signal transmitted from the camera into a digital signal; and an image data processing unit for processing the image data and detecting the defects on the pad, wherein the image data processing unit calculates one or more quantitative characteristic values of light based on the image data on any one of the points which are acquired from the image data acquisition device, and determines a location on the pad, where a difference between a level value obtained by combining one or more of the acquired quantitative characteristic values and a level value obtained from a normal surface of the pad is greater than a predetermined value, as a defect.

Notwithstanding, the apparatus and method described by Park et al. are designed for the inspection of completed chemical mechanical polishing pads that are in a ready for polishing configuration using reflected light. The use of reflected light for inspecting chemical mechanical polishing pads and the polishing layers incorporated into such pads, in particular, has significant drawbacks. The use of reflected light has limited capability to identify subsurface defects in the incorporated polishing layers, which defects are not proximate to the surface of the polishing layer. Nevertheless, as a chemical mechanical polishing pad is used, the surface of the polishing layer is gradually worn down. Hence, defects that were distant from the surface of a polishing layer of a given chemical mechanical polishing pad initially, will become increasingly more proximate to the polishing surface during the useful life of the pad. Moreover, chemical mechanical polishing pads in a ready for polishing configuration conventionally include modifications to the polishing surface of the polishing layer to facilitate polishing of a substrate (e.g., grooves, perforations), which modifications complicate automated defect detection using gray scale as described by Park et al.

Accordingly, there remains a need for improved methods of manufacturing low defect, chemical mechanical polishing pads having polishing layers using automated inspection devices and methods with enhanced polishing layer defect identification capabilities.

The present invention provides a polishing layer analyzer for analyzing polymeric sheets for use as polishing layers in chemical mechanical polishing pads, the polishing layer analyzer comprising: a magazine; and, a plurality of chucks, wherein each chuck in the plurality of chucks: (a) comprises: a central transparent section with a top surface, a bottom surface and a peripheral edge; wherein the top surface is substantially parallel with the bottom surface; and, wherein the top surface is substantially smooth; and, a holding region, surrounding the peripheral edge of the central transparent section; wherein the holding region comprises a contacting surface, a plurality of concentric grooves, and a plurality of vacuum ports; wherein the plurality of vacuum ports are in communication with the plurality of concentric grooves to facilitate applying of a vacuum to the plurality of concentric grooves; wherein the contacting surface is substantially planar with the top surface of the central transparent section; wherein the plurality of concentric grooves have a groove width, W, and a groove pitch, P; and, wherein W<P; and, (b) is configured to hold a polymeric sheet substantially flat against the top surface of the central transparent section; wherein the polymeric sheet (i) comprises: a polymer microelement composite, comprising: a polymer and a plurality of microelements, wherein the plurality of microelements are dispersed in the polymer; and, (ii) has a transmission surface, an impinging surface and a thickness, $T_S$, between the transmission surface and the impinging surface; wherein the transmission surface and the impinging surface are substantially parallel; wherein the magazine has a capacity for storing the plurality of chucks; and, wherein the magazine is designed to load, store and dispense the plurality of chucks to facilitate an analysis of a plurality of polymeric sheets.

The present invention provides a polishing layer analyzer for analyzing polymeric sheets for use as polishing layers in chemical mechanical polishing pads, the polishing layer analyzer comprising: a magazine; and, a plurality of chucks, wherein each chuck in the plurality of chucks: (a) comprises: a central transparent section with a top surface, a bottom surface and a peripheral edge; wherein the top surface is substantially parallel with the bottom surface; and, wherein the top surface is substantially smooth; and, a holding region, surrounding the peripheral edge of the central transparent section; wherein the holding region comprises a contacting surface, a plurality of concentric grooves, and a plurality of vacuum ports; wherein the plurality of vacuum ports are in communication with the plurality of concentric grooves to facilitate applying of a vacuum to the plurality of concentric grooves; wherein the contacting surface is substantially planar with the top surface of the central transparent section; wherein the plurality of concentric grooves have a groove width, W, and a groove pitch, P; and, wherein W<P; and, (b) is configured to hold a polymeric sheet substantially flat against the top surface of the central transparent section; wherein the polymeric sheet (i) comprises: a polymer microelement composite, comprising: a polymer and a plurality of microelements, wherein the plurality of microelements are dispersed in the polymer; and, (ii) has a transmission surface, an impinging surface and a thickness, $T_S$, between the transmission surface and the impinging surface; wherein the transmission surface and the impinging surface are substantially parallel; a sequencer; a light source, wherein the light source emits a beam; a light detector; a digital image data acquisition device coupled to the light detector; and, an image data processing unit coupled to the digital image data acquisition device; wherein the magazine has a capacity for storing the plurality of chucks; wherein the magazine is designed to load, store and dispense the plurality of chucks to facilitate an analysis of a plurality of polymeric sheets; wherein the sequencer is configured to extract from the magazine and convey the plurality of chucks, one at a time, to a position interposed between the light source and the light detector; wherein the beam emitted from the light source is oriented to pass through the central transparent section and impinge on the impinging surface; and, wherein the light detector is oriented to detect a transmitted light from the beam that is transmitted through the central transparent section and the thickness, $T_S$, and out the transmission surface; wherein the light detector is configured to convert an intensity of the transmitted light into an electrical signal; wherein the digital image data acquisition device coupled to the light detector is configured to covert the electrical signal from the light detector into a digital signal; wherein the image data processing unit coupled to the digital image data acquisition device is configured to process the digital signal from the digital image data acquisition device to detect macro inhomogeneities and to classify polymeric sheets as either acceptable for use as a polishing layer in a chemical mechanical polishing pad, or as suspect; wherein the plurality of polymeric sheets is divided into a population of acceptable sheets and a population of suspect sheets.

The present invention provides a method for analyzing polymeric sheets for use as polishing layers in chemical mechanical polishing pads, comprising: providing a plurality of polymeric sheets, wherein each polymeric sheet in the plurality of polymeric sheets (i) comprises: a polymer microelement composite, comprising: a polymer and a plurality of microelements, wherein the plurality of microelements are dispersed in the polymer; and, (ii) has a transmission surface, an impinging surface and a thickness, $T_S$, between the transmission surface and the impinging surface; wherein the transmission surface and the impinging surface are substantially parallel; providing a polishing layer analyzer, comprising: a magazine; and, a plurality of chucks, wherein each chuck in the plurality of chucks: (a) comprises: a central transparent section with a top surface, a bottom surface and a peripheral edge; wherein the top surface is substantially parallel with the bottom surface; and, wherein the top surface is substantially smooth; and, a holding region, surrounding the peripheral edge of the central transparent section; wherein the holding region comprises a contacting surface, a plurality of concentric grooves, and a plurality of vacuum ports; wherein the plurality of vacuum ports are in communication with the plurality of concentric grooves to facilitate applying of a vacuum to the plurality of concentric grooves; wherein the contacting surface is substantially planar with the top surface of the central transparent section; wherein the plurality of concentric grooves have a groove width, W, and a groove pitch, P; and, wherein W<P; and, (b) is configured to hold a single polymeric sheet from the plurality of polymeric sheets substantially flat against the top surface of the central transparent section; a light source, wherein the light source emits a beam; a light detector; a digital image data acquisition device; and, an image data processing unit; pairing the plurality of polymeric sheets with the plurality of chucks to provide a plurality of sheeted chucks; wherein each sheeted chuck in the plurality of sheeted chucks comprises an associated polymeric sheet held thereto by the holding region such that the impinging surface of the associated polymeric sheet is held flat against the top surface; conveying the plurality of sheeted chucks, one at a time, between the light source and the light detector; wherein the beam emitted from the light source is oriented to pass through the central transparent section and impinge on the impinging surface; and, wherein the light detector is oriented to detect a transmitted light from the beam that is transmitted through the central transparent section and the thickness, $T_S$, and out the transmission surface; wherein the transmitted light has at least one detectable property; wherein the at least one detectable property includes an intensity of the transmitted light; wherein the intensity of the transmitted light is converted into an electrical signal by the light detector; wherein the electrical signal from the light detector is converted into a digital signal by the digital image data acquisition device; and, wherein the digital signal from the digital image data acquisition device is processed by the image data processing unit, wherein the image data processing unit is configured to detect macro inhomogeneities and to classify polymeric sheets as either acceptable or suspect; and, wherein the plurality of polymeric sheets is divided into a population of acceptable sheets and a population of suspect sheets.

DETAILED DESCRIPTION

The method of the present invention provides significant improvement in the quality of finished (ready for use) chemical mechanical polishing pads. The method of the present invention greatly enhances the quality control aspects of chemical mechanical polishing pad production using polymeric sheets formed from a polymer microelement composite, comprising a polymer and a plurality of microelements dispersed in the polymer by performing a first inspection of the polymeric sheets to identify acceptable sheets from a plurality of polymeric sheets and mapping the transmission surfaces of suspect sheets to facilitate focused visual inspection of macro inhomogeneity containing portions of the suspect sheets. In this way, operator fatigue is greatly reduced (i.e., operators are not required to spend long hours staring at polymeric sheets to locate macro inhomogeneities). Hence, enabling increased operator focus where it brings the most value (i.e., evaluating specific inhomogeneities in polymeric sheets to determine suitability for use).

The term "poly(urethane)" as used herein and in the appended claims encompasses (a) polyurethanes formed from the reaction of (i) isocyanates and (ii) polyols (including diols); and, (b) poly(urethane) formed from the reaction of (i) isocyanates with (ii) polyols (including diols) and (iii) water, amines or a combination of water and amines.

Figure 1:
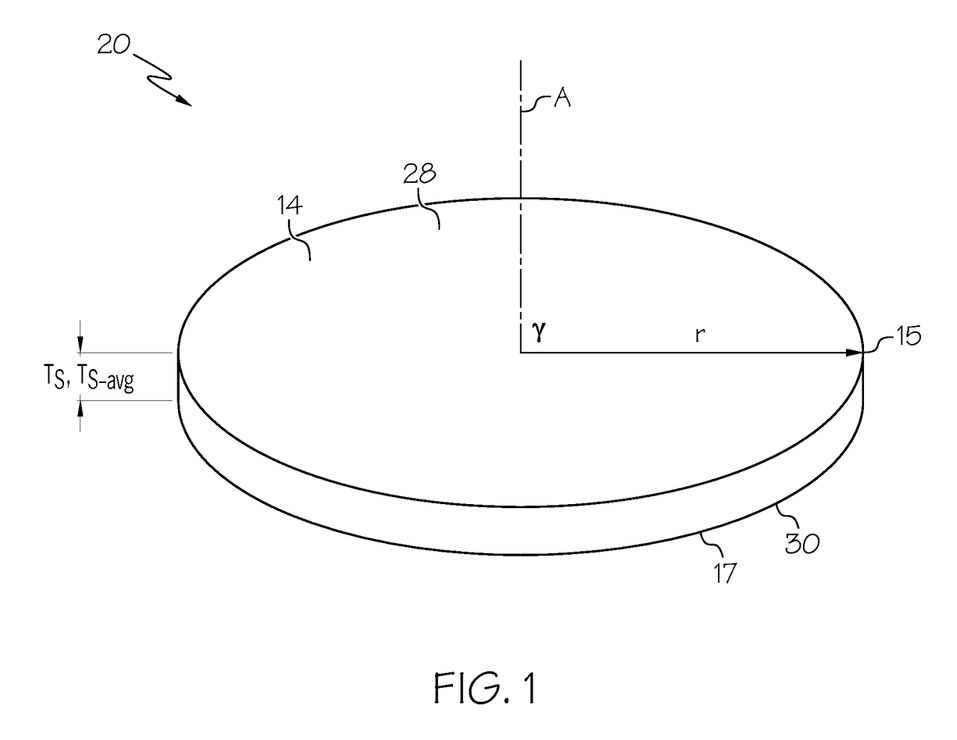
FIG. 1 is a depiction of a perspective view of a polymeric sheet.
Figure 2:
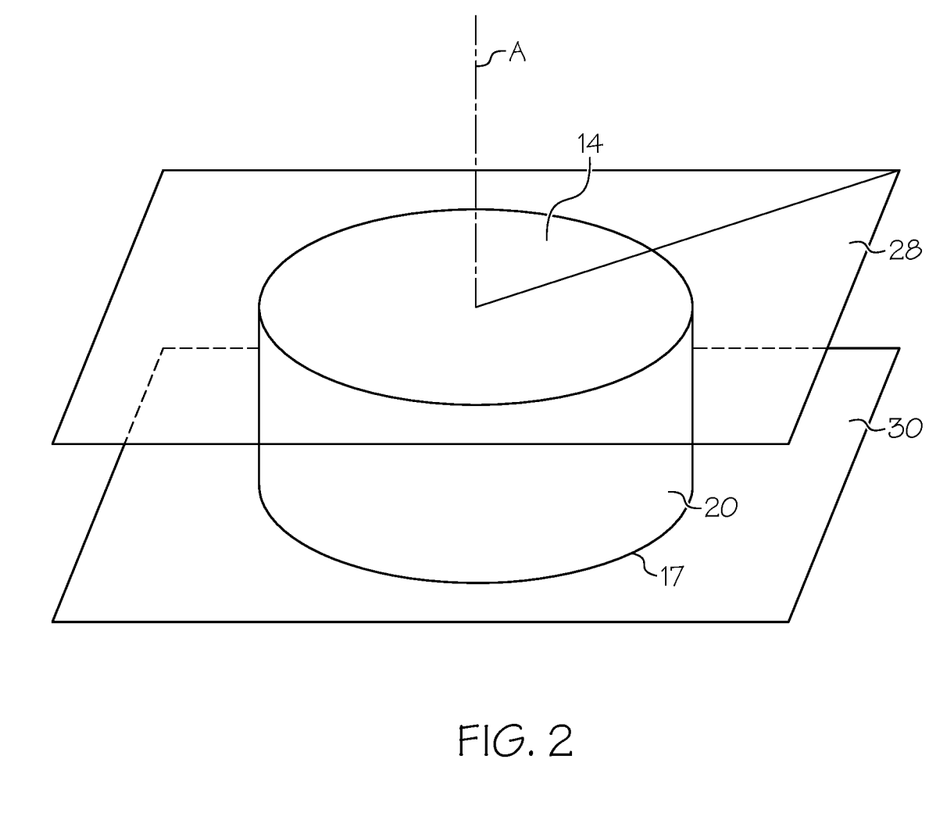
FIG. 2 is a depiction of a perspective view of a polymeric sheet.
Figure 3:
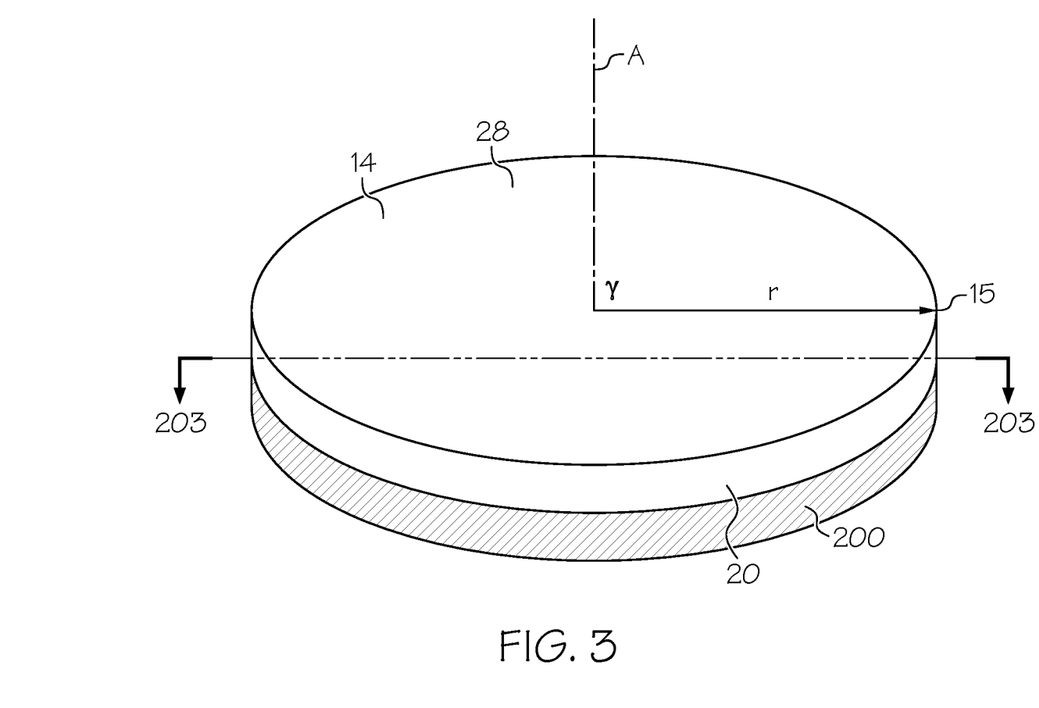
FIG. 3 is a depiction of a perspective view of a polymeric sheet held flat against the top surface of a chuck.
Figure 4:
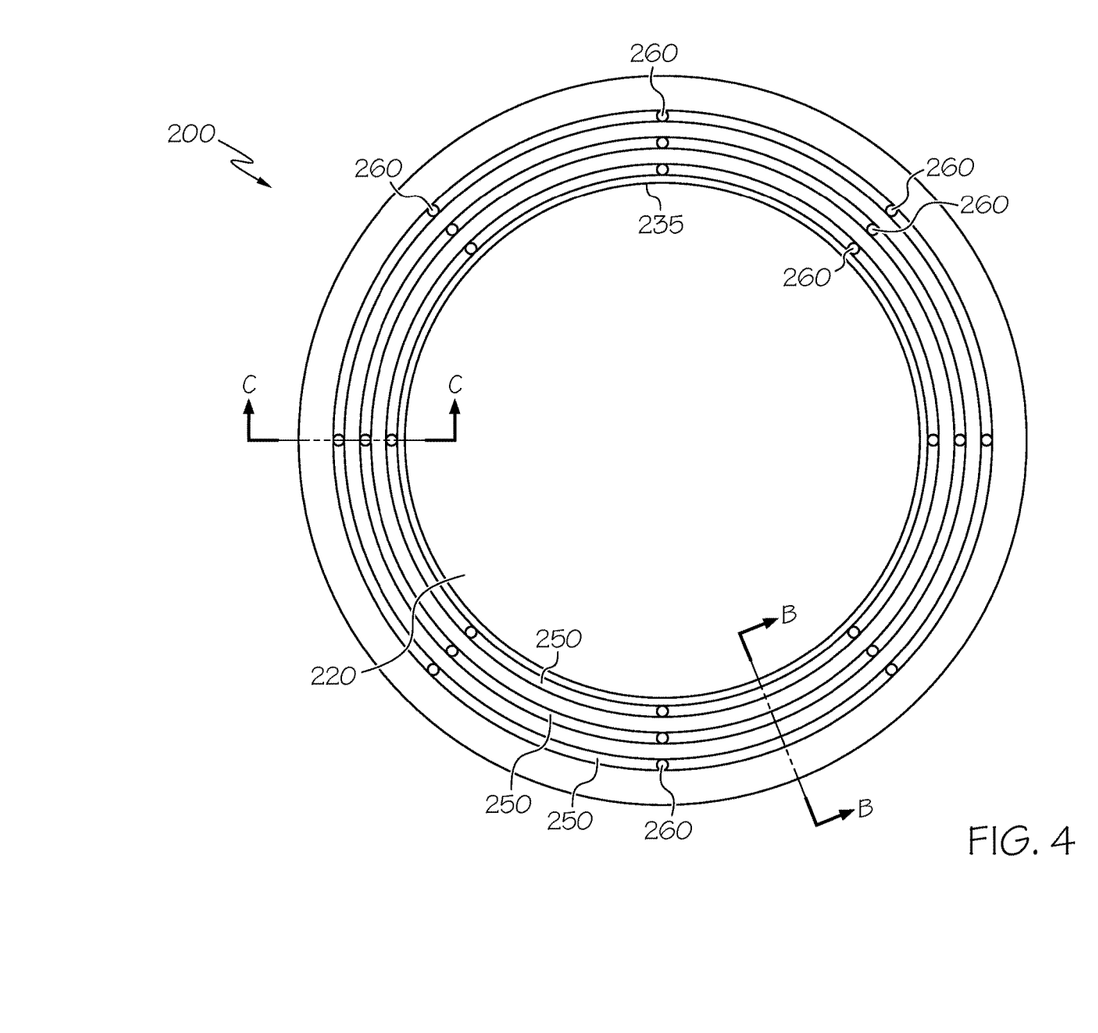
FIG. 4 is a depiction of a top plan view of a chuck taken along line 203-203 in FIG. 3.
Figure 5:
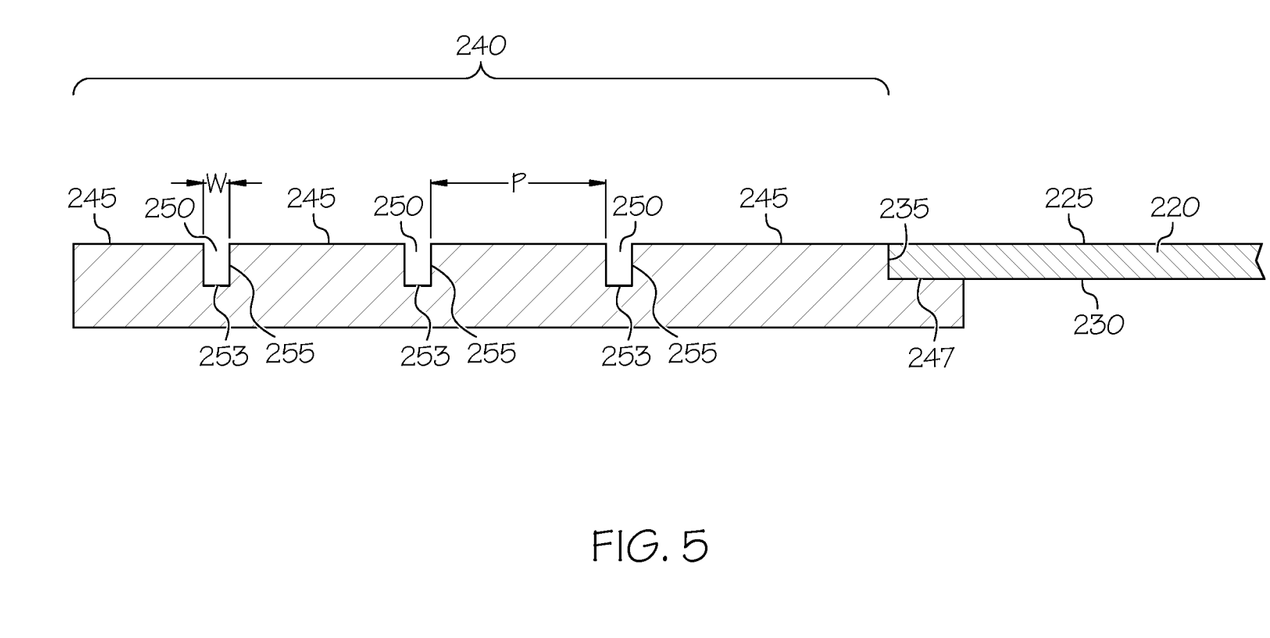
FIG. 5 is a cross sectional view taken along line B-B in FIG. 4.
Figure 6:
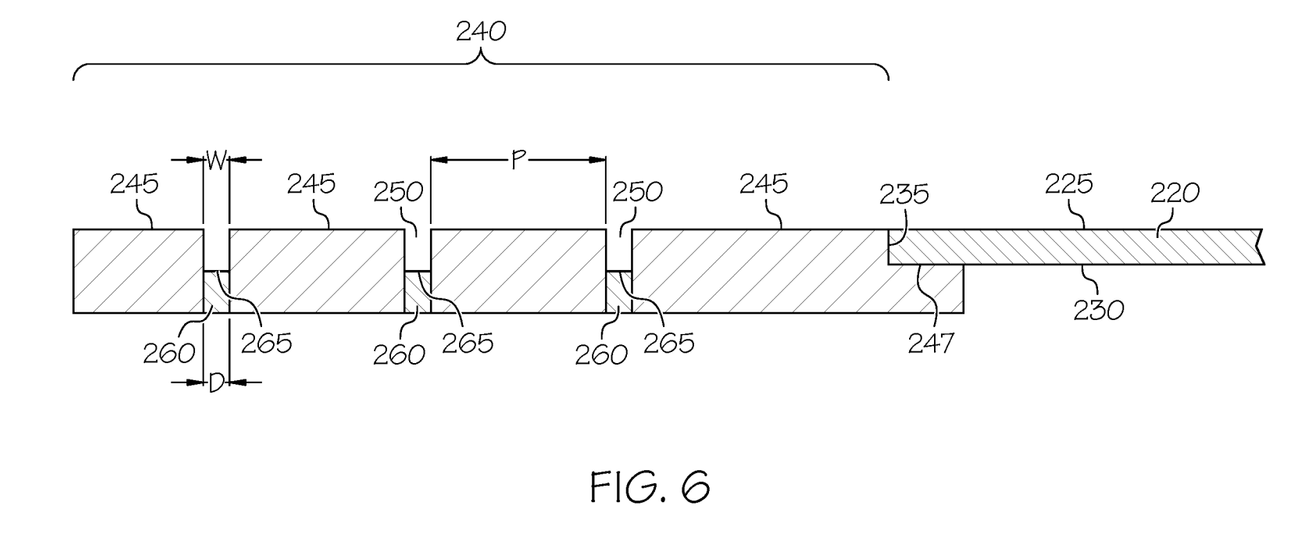
FIG. 6 is a cross sectional view taken along line C-C in FIG. 4.

The term "average polymeric sheet thickness, $T_{S-avg}$" as used herein and in the appended claims in reference to a polymeric sheet (20) having a transmission surface (14) and an impinging surface (17) means the average of the thickness, $T_S$, of the polymeric sheet (20) measured in a direction normal to the plane (28) of the transmission surface (14) from the transmission surface (14) to the impinging surface (17) of the polymeric sheet (20). (See FIGS. 1-2).

The term "average base layer thickness, $T_{B-avg}$" as used herein and in the appended claims in reference to a chemical mechanical polishing pad (110) having a subpad (125) interfaced with a polymeric sheet incorporated as a polishing layer (120) having a polishing surface (114) means the average of the thickness, $T_B$, of the subpad (125) measured in a direction normal to the polishing surface (114) from the bottom surface (127) of the subpad (125) to the top surface (126) of the subpad (125). (See FIG. 7).

The term "average total thickness, $T_{T-avg}$" as used herein and in the appended claims in reference to a chemical mechanical polishing pad (110) having a polymeric sheet incorporated as a polishing layer (120) having a polishing surface (114) means the average of the thickness, $T_T$, of the chemical mechanical polishing pad (110) measured in a direction normal to the polishing surface (114) from the polishing surface (114) to the bottom surface (127) of the subpad (125). (See FIG. 7).

The term "substantially circular cross section" as used herein and in the appended claims in reference to a polymeric sheet (20) means that the longest radius, r, of the polymeric sheet (20) projected onto the plane (28) of the transmission surface (14) of the polymeric sheet (20) from a central axis, A, to the outer perimeter (15) of the polymeric sheet (20) is ≤20% longer than the shortest radius, r, of the polymeric sheet (20) projected onto the plane (28) of the transmission surface (14) of the polymeric sheet (20) from the central axis, A, to the outer perimeter (15) of the polymeric sheet (20). (See FIGS. 1 & 2).

The term "substantially parallel" as used herein and in the appended claims in reference to a polymeric sheet (20) means that the central axis, A, (and any lines parallel therewith) normal to a plane (30) of the impinging surface (17) of the polymeric sheet (20) will intersect a plane (28) of the transmission surface (14) at an angle, γ; wherein the angle, γ, is between 89 and 91°. (See FIGS. 1 & 2).

The term "substantially smooth" as used herein and in the appended claims means that the surface is flat to ±0.001 mm.

The term "substantially planar" as used herein and in the appended claims means that the referenced surfaces planar to ±0.001 mm.

The term "substantially flat" as used herein and in the appended claims in reference to a polymeric sheet held against a top surface of a central transparent section of a chuck means that the transmission surface of the polymeric sheet is flat to ±1 mm.

The term "substantially circular" as used herein and in the appended claims in reference to a central transparent section (220) of chuck (200) means that the peripheral edge (235) has a circularity of ≥0.6. (See FIGS. 3-6).

The term "essentially circular" as used herein and in the appended claims in reference to a central transparent section (220) of chuck (200) means that the peripheral edge (235) has a circularity of ≥0.9. (See FIGS. 3-6).

The term "rigid material" as used herein and in the appended claims in reference to a material of construction of a holding region (240) of a chuck (200) means the material of construction does not deform under the conditions of its intended use herein.

The term "macro inhomogeneity" as used herein and in the appended claims means a localized region on the transmission surface of a polymeric sheet surrounded by an adjacent region on the transmission surface of the polymeric sheet, wherein the detected intensity of light transmitted through the localized region is higher or lower than the detected intensity of light transmitted through the adjacent region by an amount of ≥0.1% of the detectable intensity range of the light detector; and, wherein the localized region encompasses a portion of the transmission surface large enough to occlude a circle having a diameter of 15.875 mm in the plane of the transmission surface.

The term "density defect" as used herein and in the appended claims refers to a macro inhomogeneity in a polymeric sheet with a significantly reduced microelement concentration relative to the surrounding region of the polymeric sheet. Density defects exhibit a markedly higher transparency (i.e., higher detected intensity of light transmitted) compared with the surrounding region of the polymeric sheet.

The term "air hole" as used herein and in the appended claims refers to a macro inhomogeneity in a polymeric sheet with an air inclusion resulting in a markedly higher transparence (i.e., higher detected intensity of light transmitted) compared with the surrounding region of the polymeric sheet.

The term "inclusion defect" as used herein and in the appended claims refers to a macro inhomogeneity in a polymeric sheet with a foreign contaminant resulting in a markedly lower transparence (i.e., lower detected intensity of light transmitted) compared with the surrounding region of the polymeric sheet.

Preferably, the polishing layer analyzer of the present invention comprises: a magazine; and, a plurality of chucks, wherein each chuck in the plurality of chucks: (a) comprises:

a central transparent section (preferably, wherein the central transparent section is a right cylindrical transparent section) (220) with a top surface (225), a bottom surface (230) and a peripheral edge (235); wherein the top surface is substantially parallel with the bottom surface; (preferably, wherein the peripheral edge is substantially circular; more preferably, wherein the peripheral edge is essentially circular); and, wherein the top surface is substantially smooth; and, a holding region (240), surrounding the peripheral edge of the central transparent section; wherein the holding region (240) comprises a contacting surface (245), a plurality of concentric grooves (250), and a plurality of vacuum ports (260); wherein the plurality of vacuum ports are in communication with the plurality of concentric grooves (250) to facilitate applying of a vacuum to the plurality of concentric grooves (250); wherein the contacting surface (245) is substantially planar with the top surface (225) of the central transparent section (220); wherein the plurality of concentric grooves (250) have a groove width, W, and a groove pitch, P; and, wherein W<P (preferably, wherein W<½ P; more preferably, wherein W<⅓ P; most preferably, wherein W<¼ P); and, (b) is configured to hold a polymeric sheet substantially flat against the top surface (225) of the central transparent section (220); wherein the polymeric sheet (i) comprises: a polymer microelement composite, comprising: a polymer and a plurality of microelements, wherein the plurality of microelements are dispersed in the polymer; and, (ii) has a transmission surface, an impinging surface and a thickness, $T_S$, between the transmission surface and the impinging surface; wherein the transmission surface and the impinging surface are substantially parallel; wherein the magazine has a capacity for storing the plurality of chucks; and, wherein the magazine is designed to load, store and dispense the plurality of chucks to facilitate an analysis of a plurality of polymeric sheets. (See FIGS. 3-6).

Preferably, the magazine is designed to hold, store and dispense a plurality of chucks. More preferably, the magazine is designed to hold, store and dispense a plurality of chucks, wherein each chuck in the plurality of chucks is associated with a polymeric sheet such that the polymeric sheet is held substantially flat against the top surface of its central transparent section. Preferably, the magazine has a design capacity for holding at least 10 chucks with associated polymeric sheets (more preferably, at least 15 chucks with associated polymeric sheets; still more preferably, at least 20 chucks with associated polymeric sheets; most preferably, at least 30 chucks with associated polymeric sheets). The magazine design capacity enables an operator to load a plurality of chucks with associated polymeric sheets into an automated inspection system. Once the plurality of chucks with associated polymeric sheets are loaded into the magazine, the operator is able to then perform other tasks while the automated inspection system processes and classifies the associated polymeric sheets as either acceptable or suspect.

Preferably, each chuck (200) has a holding region (240), surrounding the peripheral edge (235) of the central transparent section (220); wherein the holding region (240) has a contacting surface (245), a plurality of concentric grooves (250), and a plurality of vacuum ports (260); wherein each concentric groove (250) has a pair of sidewalls (255) and a base (253). More preferably, each chuck (200) has a holding region (240), surrounding the peripheral edge (235) of the central transparent section (220); wherein the holding region (240) has a contacting surface (245), a plurality of concentric grooves (250), and a plurality of vacuum ports (260); wherein each concentric groove (250) has a pair of sidewalls (255) and a base (253); wherein each sidewall (255) is substantially perpendicular to the contacting surface (245).

Preferably, each chuck (200) has a holding region (240), surrounding the peripheral edge (235) of the central transparent section (220); wherein the holding region (240) has a contacting surface (245), a plurality of concentric grooves (250), and a plurality of vacuum ports (260); wherein the plurality of vacuum ports are in communication with the plurality of concentric grooves (250) to facilitate applying of a vacuum to the plurality of concentric grooves (250); and, wherein each concentric groove (250) has at least one vacuum port (260) in communication therewith to facilitate pulling of a vacuum therein when a polymeric sheet (20) is disposed against the holding region (240). (See FIG. 3). More preferably, each concentric groove (250) has 4 to 20 vacuum ports (260). Most preferably, each concentric groove (250) has 4 to 20 vacuum ports (260) evenly distributed along the base (253) of each concentric groove (250). Preferably, each vacuum port (260) has an opening (265) in the base (253) of the concentric groove (250). Preferably, each opening (265) in the base (253) of the concentric groove (250) has a circular cross section with a diameter, D; wherein 0.75*W≤D≤W (preferably, wherein 0.9*W≤D≤W; more preferably, wherein 0.95*W≤D≤W; most preferably, wherein D=W).

Preferably, each chuck (200) has a holding region (240); wherein the holding region (240) is constructed of a rigid material. Preferably, the holding region (240) is constructed of a material selected from the group consisting of metals; stone materials (e.g., granite and marble); ceramic materials; and hard plastics (e.g., aliphatic polyamides such as Nylon 6-6). More preferably, the holding region (240) is constructed of a material selected from the group consisting of a metal alloy. Still more preferably, the holding region (240) is constructed of a metal alloy, wherein the metal alloy is selected from the group consisting of alloys of aluminum, alloys of carbon (e.g., tool steel), alloys of iron, alloys of nickel (e.g., stainless steels (such as, 304 stainless steel, 316 stainless steel); Hastelloys®[1] (such as, Hastelloy®-C)); and, alloys of titanium. Most preferably, the holding region (240) is constructed of a metal alloy, wherein the metal alloy is a stainless steel (e.g., 304 stainless steel, 316 stainless steel).

[1] Hastelloy is a registered trademark of Haynes International, Inc. and encompasses a variety of corrosion-resistant nickel containing metal alloys.

Preferably, each chuck (200) has a central transparent section (220), wherein the central transparent section (220) has a transmittance of ≥90% for the beam emitted from the light source. More preferably, each chuck (200) has a central transparent section (220), wherein the central transparent section (220) has a transmittance of ≥90% for light having a wavelength of 440 to 490 nm.

Preferably, each chuck (200) has a central transparent section (220) that is made of a material selected from the glass, quartz and plastic. More preferably, each chuck (200) has a central transparent section (220) that is made of a material selected from glass and quartz. Most preferably, each chuck (200) has a central transparent section (220) that is made of glass.

Preferably, each chuck (200) has a holding region (240), wherein the holding region (240) is an annulus.

Preferably, each chuck (200) has a holding region (240), wherein the holding region (240) further comprises a ledge (247) extending from the peripheral edge (235) of the central transparent section (220) along a portion of the bottom surface (230). More preferably, each chuck (200) has a holding region (240), wherein the holding region (240) further comprises a ledge (247) extending from the peripheral edge (235) of the central transparent section (220) along a portion of the bottom surface (230) and wherein the central transparent section (220) is secured to the ledge (247) of the holding region (240) with an adhesive. (See FIGS. 5-6).

Each chuck (200), in the plurality of chucks, is configured to hold a polymeric sheet (20) substantially flat against the top surface (225) of the central transparent section (220); wherein the polymeric sheet (20) (i) comprises: a polymer microelement composite, comprising: a polymer and a plurality of microelements, wherein the plurality of microelements are dispersed in the polymer; and, (ii) has a transmission surface (14), an impinging surface (17) and a thickness, $T_S$, between the transmission surface (14) and the impinging surface (17); wherein the transmission surface (14) and the impinging surface (17) are substantially parallel. Preferably, each polymeric sheet (20) has an average thickness, $T_{S\text{-}avg}$, of 500 to 5,000 μm (preferably, 750 to 4,000 μm; more preferably, 1,000 to 3,000 μm; most preferably, 1,200 to 2,100 μm). Preferably, each polymeric sheet (20) has an average radius, $r_{avg}$, of 20 to 100 cm (more preferably, of 25 to 65 cm; most preferably, of 40 to 60 cm). (See FIGS. 1-3).

Preferably, each polymeric sheet (20) comprises a polymer microelement composite; wherein the polymer microelement composite, comprises: a polymer and a plurality of microelements; and, wherein the plurality of microelements are dispersed in the polymer. Preferably, the polymer microelement composite comprises: a polymer and a plurality of microelements, wherein the plurality of microelements are dispersed in the polymer in a pattern. More preferably, the polymer microelement composite comprises: a polymer and a plurality of microelements, wherein the plurality of microelements are dispersed in the polymer in a pattern selected from the group consisting of a uniform pattern and a gradient pattern. Most preferably, the polymer microelement composite comprises: a polymer and a plurality of microelements, wherein the plurality of microelements are uniformly dispersed in the polymer. Preferably, the polymer microelement composite is prepared using a liquid prepolymer, wherein the plurality of microelements are dispersed in the liquid prepolymer; and, wherein the liquid prepolymer is then cured to form the polymer.

Preferably, the liquid prepolymer used in the preparation of the polymer microelement composite polymerizes to form a material selected from poly(urethane), polysulfone, polyether sulfone, nylon, polyether, polyester, polystyrene, acrylic polymer, polyurea, polyamide, polyvinyl chloride, polyvinyl fluoride, polyethylene, polypropylene, polybutadiene, polyethylene imine, polyacrylonitrile, polyethylene oxide, polyolefin, poly(alkyl)acrylate, poly(alkyl)methacrylate, polyamide, polyether imide, polyketone, epoxy, silicone, polymer formed from ethylene propylene diene monomer, protein, polysaccharide, polyacetate and a combination of at least two of the foregoing. Preferably, the liquid prepolymer used in the preparation of the polymer microelement composite polymerizes to form a material comprising a poly(urethane). More preferably, the liquid prepolymer used in the preparation of the polymer microelement composite polymerizes to form a material comprising a polyurethane. Most preferably, the liquid prepolymer used in the preparation of the polymer microelement composite polymerizes (cures) to form a polyurethane.

Preferably, the liquid prepolymer used in the preparation of the polymer microelement composite comprises a polyisocyanate-containing material. More preferably, the liquid prepolymer used in the preparation of the polymer microelement composite comprises the reaction product of a polyisocyanate (e.g., diisocyanate) and a hydroxyl-containing material.

Preferably, the polyisocyanate used in the preparation of the polymer microelement composite is selected from methylene bis 4,4'-cyclohexyl-isocyanate; cyclohexyl diisocyanate; isophorone diisocyanate; hexamethylene diisocyanate; propylene-1,2-diisocyanate; tetramethylene-1,4-diisocyanate; 1,6-hexamethylene-diisocyanate; dodecane-1,12-diisocyanate; cyclobutane-1,3-diisocyanate; cyclohexane-1,3-diisocyanate; cyclohexane-1,4-diisocyanate; 1-isocyanato-3,3,5-trimethyl-5-isocyanatomethylcyclohexane; methyl cyclohexylene diisocyanate; triisocyanate of hexamethylene diisocyanate; triisocyanate of 2,4,4-trimethyl-1,6-hexane diisocyanate; urtdione of hexamethylene diisocyanate; ethylene diisocyanate; 2,2,4-trimethylhexamethylene diisocyanate; 2,4,4-tri-methylhexamethylene diisocyanate; dicyclohexylmethane diisocyanate; and combinations thereof. Most preferably, the polyisocyanate used in the preparation of the polymer microelement composite is aliphatic and has less than 14 percent unreacted isocyanate groups.

Preferably, the hydroxyl-containing material used with the present invention is a polyol. Exemplary polyols include, for example, polyether polyols, hydroxy-terminated polybutadiene (including partially and fully hydrogenated derivatives), polyester polyols, polycaprolactone polyols, polycarbonate polyols, and mixtures thereof.

Preferred polyols include polyether polyols. Examples of polyether polyols include polytetramethylene ether glycol ("PTMEG"), polyethylene propylene glycol, polyoxypropylene glycol, and mixtures thereof. The hydrocarbon chain can have saturated or unsaturated bonds and substituted or unsubstituted aromatic and cyclic groups. Preferably, the polyol of the present invention includes PTMEG. Suitable polyester polyols include, but are not limited to, polyethylene adipate glycol; polybutylene adipate glycol; polyethylene propylene adipate glycol; o-phthalate-1,6-hexanediol; poly(hexamethylene adipate) glycol; and mixtures thereof. The hydrocarbon chain can have saturated or unsaturated bonds, or substituted or unsubstituted aromatic and cyclic groups. Suitable polycaprolactone polyols include, but are not limited to, 1,6-hexanediol-initiated polycaprolactone; diethylene glycol initiated polycaprolactone; trimethylol propane initiated polycaprolactone; neopentyl glycol initiated polycaprolactone; 1,4-butanediol-initiated polycaprolactone; PTMEG-initiated polycaprolactone; and mixtures thereof. The hydrocarbon chain can have saturated or unsaturated bonds, or substituted or unsubstituted aromatic and cyclic groups. Suitable polycarbonates include, but are not limited to, polyphthalate carbonate and poly(hexamethylene carbonate) glycol.

Preferably, the plurality of microelements used in the preparation of the polymer microelement composite are selected from gas bubbles, hollow core polymeric materials (i.e., microspheres), liquid filled hollow core polymeric materials, water soluble materials (e.g., cyclodextrin) and an insoluble phase material (e.g., mineral oil). Preferably, the plurality of microelements used in the preparation of the polymer microelement composite are microspheres, such as, polyvinyl alcohols, pectin, polyvinyl pyrrolidone, hydroxyethylcellulose, methylcellulose, hydropropylmethylcellulose, carboxymethylcellulose, hydroxypropylcellulose, polyacrylic acids, polyacrylamides, polyethylene glycols, polyhydroxyetheracrylites, starches, maleic acid copolymers, polyethylene oxide, polyurethanes, cyclodextrin and combinations thereof (e.g., Expancel™ from Akzo Nobel of Sundsvall, Sweden). The microspheres can be chemically modified to change the solubility, swelling and other properties by branching, blocking, and crosslinking, for example. Preferably, the microspheres have a mean diameter that is less than 150 µm, and more preferably a mean diameter of less than 50 µm. Most preferably, the microspheres have a mean diameter that is less than 15 µm. Note, the mean diameter of the microspheres can be varied and different sizes or mixtures of different microspheres 48 can be used. A most preferred material for the microspheres is a copolymer of acrylonitrile and vinylidene chloride (e.g., Expancel® available from Akzo Nobel).

The liquid prepolymer used in the preparation of the polymer microelement composite of the present invention, optionally further comprises a curing agent. Preferred curing agents include diamines. Suitable polydiamines include both primary and secondary amines. Preferred polydiamines include, but are not limited to, diethyl toluene diamine ("DETDA"); 3,5-dimethylthio-2,4-toluenediamine and isomers thereof; 3,5-diethyltoluene-2,4-diamine and isomers thereof (e.g., 3,5-diethyltoluene-2,6-diamine); 4,4'-bis-(sec-butylamino)-diphenylmethane; 1,4-bis-(sec-butylamino)-benzene; 4,4'-methylene-bis-(2-chloroaniline); 4,4'-methylene-bis-(3-chloro-2,6-diethylaniline) ("MCDEA"); polytetramethyleneoxide-di-p-aminobenzoate; N,N'-dialkyldiamino diphenyl methane; p,p'-methylene dianiline ("MDA"); m-phenylenediamine ("MPDA"); methylene-bis 2-chloroaniline ("MBOCA"); 4,4'-methylene-bis-(2-chloroaniline) ("MOCA"); 4,4'-methylene-bis-(2,6-diethylaniline) ("MDEA"); 4,4'-methylene-bis-(2,3-dichloroaniline) ("MDCA"); 4,4'-diamino-3,3'-diethyl-5,5'-dimethyl diphenylmethane, 2,2',3,3'-tetrachloro diamino diphenylmethane; trimethylene glycol di-p-aminobenzoate; and mixtures thereof. Preferably, the diamine curing agent is selected from 3,5-dimethylthio-2,4-toluenediamine and isomers thereof.

Curing agents can also include diols, triols, tetraols and hydroxy-terminated curatives. Suitable diols, triols, and tetraol groups include ethylene glycol; diethylene glycol; polyethylene glycol; propylene glycol; polypropylene glycol; lower molecular weight polytetramethylene ether glycol; 1,3-bis(2-hydroxyethoxy) benzene; 1,3-bis-[2-(2-hydroxyethoxy) ethoxy]benzene; 1,3-bis-{2-[2-(2-hydroxyethoxy) ethoxy]ethoxy}benzene; 1,4-butanediol; 1,5-pentanediol; 1,6-hexanediol; resorcinol-di-(beta-hydroxyethyl) ether; hydroquinone-di-(beta-hydroxyethyl) ether; and mixtures thereof. Preferred hydroxy-terminated curatives include 1,3-bis(2-hydroxyethoxy) benzene; 1,3-bis-[2-(2-hydroxyethoxy) ethoxy]benzene; 1,3-bis-{2-[2-(2-hydroxyethoxy) ethoxy]ethoxy}benzene; 1,4-butanediol; and mixtures thereof. The hydroxy-terminated and diamine curatives can include one or more saturated, unsaturated, aromatic, and cyclic groups. Additionally, the hydroxy-terminated and diamine curatives can include one or more halogen groups.

Preferably, the polishing layer analyzer of the present invention further comprises: a sequencer; a light source, wherein the light source emits a beam; a light detector; a digital image data acquisition device coupled to the light detector; and, an image data processing unit coupled to the digital image data acquisition device; wherein the sequencer is configured to extract from the magazine and convey the plurality of chucks, one at a time, to a position interposed between the light source and the light detector; wherein the beam emitted from the light source is oriented to pass through the central transparent section and impinge on the impinging surface; and, wherein the light detector is oriented to detect a transmitted light from the beam that is transmitted through the central transparent section and the thickness, $T_S$, and out the transmission surface; wherein the light detector is configured to convert an intensity of the transmitted light into an electrical signal; wherein the digital image data acquisition device coupled to the light detector is configured to covert the electrical signal from the light detector into a digital signal; wherein the image data processing unit coupled to the digital image data acquisition device is configured to process the digital signal from the digital image data acquisition device to detect macro inhomogeneities and to classify polymeric sheets as either acceptable for use as a polishing layer in a chemical mechanical polishing pad, or as suspect; wherein the plurality of polymeric sheets is divided into a population of acceptable sheets and a population of suspect sheets.

Preferably, the sequencer is configured to load and extract chucks from the magazine. Preferably, the sequencer is configured to load and extract chucks from the magazine one at a time. Preferably, the sequencer is further configured to convey chucks with associated polymeric sheets, one at a time, to a position interposed between a light source and a light detector; and, returning the chucks with associated polymeric sheets, one at a time, back into the magazine. Preferably, the sequencer includes at least one linear motor. More preferably, the sequencer includes at least one liner motor having a linear scale resolution of ≤1 µm.

Preferably, the light source, emits a beam. Preferably, the beam emitted by the light source exhibits an emission spectrum including wavelengths selected from at least one of the visible, ultraviolet and infrared regions. Preferably, the light source is selected from a broad band source (e.g., a white light source) and a narrow band source (e.g., a narrow band blue light source). More preferably, the light source is a narrow band blue light source. Still more preferably, the light source is a narrow band blue light source that emits a beam, wherein the beam exhibits an emission spectrum having a peak wavelength of 460 to 490 nm (preferably, 460 to 480 nm; more preferably, 460 to 470; most preferably, 463 to 467 nm) and a full width at half maximum intensity, FWHM, of ≤50 nm (preferably, ≤40 nm; more preferably, ≤35 nm; most preferably, ≤30 nm). One or ordinary skill in the art will be able to select an appropriate light source for providing a beam with an emission spectrum in the desired region. Preferably, in the method of the present invention, the automated inspection system comprises a light source, wherein the light source is a light emitting diode.

Preferably, the light detector is capable of converting at least one detectable property of a transmitted light from a beam that is transmitted through the thickness, $T_S$, and out the transmission surface of a polymeric sheet. More preferably, the light detector is capable of converting an intensity of the transmitted light from the beam that is transmitted through the thickness, $T_S$, and out the transmission surface of a polymeric sheet. Most preferably, the light detector is capable of converting an intensity and a wavelength spectrum of the transmitted light from the beam that is transmitted through the thickness, $T_S$, and out the transmission surface of a polymeric sheet. Preferably, the light detector is an optoelectric converting device, which converts the at least one detectable property of the transmitted light incident thereon into an electric signal. Preferably, the light detector is an array of charge coupled devices (CCDs). Preferably, the charge coupled devices (CCDs) used are selected from monochromatic and color CCDs. More preferably, the light detector comprises an array of at least 5 (most preferably, at least 8) optoelectric converting devices. Most preferably, the light detector comprises an array of at least 8 charge coupled devices (CCD) image sensors having a resolution of ≤20 µm (preferably, ≤16 µm) and a field of view of ≥100 mm (preferably, ≥120 mm).

Preferably, the digital image data acquisition device converts to a digital signal the electrical signal output from the light detector. Digital image data acquisition devices suitable for use with the present invention are well known in the art.

The heterogeneous compositional nature of polymeric sheets comprising a polymer microelement composite makes reference to a hypothetical standard sheet impractical. That is, the existence of various, innocuous production artifacts in such polymeric sheets make simple grayscale comparison to a standard value ineffective for use in an automated system for inspecting polymeric sheets for incorporation as polishing layers in chemical mechanical polishing pads.

General purpose and specialty purpose image data processing units suitable for use with the present invention are well known in the art. Preferably, the image data processing unit in the automated inspection system used in the present invention, comprises a central processing unit coupled to a nonvolatile data storage unit.

Preferably, the central processing unit is further coupled to one or more user input interface controllers (e.g., mouse, keyboard) and at least one output display.

Preferably, image data processing unit is configured to detect macro inhomogeneities in the polymeric sheets and to classify the polymeric sheets as either acceptable or suspect. Preferably, the classification of the polymeric sheets as acceptable or suspect is performed by the image data processing unit based on a menu of quality control criteria. A variety of defects can occur during the manufacture of the polymeric sheets including, for example, density defects, air hole defects and inclusion defects. Note that any one or a combination of these defects can constitute a macro inhomogeneity in a polymeric sheet depending on the size of the affected portion of the transmission surface. Note that the various defect types will present differently to the light detector. For density defects and air holes, the defective region will be more transparent than the surrounding region of the polymeric sheet. For inclusion defects, the defective region will be less transparent than the surrounding region of the polymeric sheet. Whether such defects are acceptable depends on a number of conditions, including, for example, the substrate for which the chemical mechanical polishing pad incorporating the polymeric sheet will be tasked for polishing. Certain substrates are more delicate than others, and hence require tighter controls on the homogeneity of the polymeric sheets to be used as polishing layers in chemical mechanical polishing pads manufactured for their polishing.

Preferably, in the polishing layer analyzer of the present invention, the image data processing unit is preferably further configured to produce and store in a nonvolatile memory a map of the at least one suspect sheet, wherein the population of suspect sheets includes at least one suspect sheet and wherein the at least one suspect sheet contains at least one detected macro inhomogeneity; wherein a location for the at least one detected macro inhomogeneity is positioned.

Preferably, in the polishing layer analyzer of the present invention, the image data processing unit is preferably further configured to produce and store in a nonvolatile memory a map of the at least one suspect sheet, wherein the population of suspect sheets includes at least one suspect sheet and wherein the at least one suspect sheet contains at least one detected macro inhomogeneity; wherein a location for the at least one detected macro inhomogeneity is positioned; and, wherein the analyzer, further comprises: a display; wherein an image of the select sheet is displayed on the display. The image displayed of the select sheet on the display can be an image of the entirety of the transmission surface of the select sheet. Preferably, the image of the select sheet is a partial image showing a magnification of at least one detected macro inhomogeneity. Preferably, the partial image of the select sheet displayed on the display includes the entirety of the macro inhomogeneity and the surrounding region of the transmission surface of the select sheet. Preferably, the partial image of the select sheet displayed on the display can be magnified to enhance the detail of the displayed image to facilitate a visual inspection of the select sheet.

Preferably, the method of the present invention for analyzing polymeric sheets for use as polishing layers in chemical mechanical polishing pads, comprises: providing a plurality of polymeric sheets, wherein each polymeric sheet in the plurality of polymeric sheets (i) comprises: a polymer microelement composite, comprising: a polymer and a plurality of microelements, wherein the plurality of microelements are dispersed in the polymer; and, (ii) has a transmission surface, an impinging surface and a thickness, $T_S$, between the transmission surface and the impinging surface; wherein the transmission surface and the impinging surface are substantially parallel; providing a polishing layer analyzer, comprising: a magazine; and, a plurality of chucks, wherein each chuck in the plurality of chucks: (a) comprises: a central transparent section with a top surface, a bottom surface and a peripheral edge; wherein the top surface is substantially parallel with the bottom surface; and, wherein the top surface is substantially smooth; and, a holding region, surrounding the peripheral edge of the central transparent section; wherein the holding region comprises a contacting surface, a plurality of concentric grooves, and a plurality of vacuum ports; wherein the plurality of vacuum ports are in communication with the plurality of concentric grooves to facilitate applying of a vacuum to the plurality of concentric grooves; wherein the contacting surface is substantially planar with the top surface of the central transparent section; wherein the plurality of concentric grooves have a groove width, W, and a groove pitch, P; and, wherein W<P; and, (b) is configured to hold a single polymeric sheet from the plurality of polymeric sheets substantially flat against the top surface of the central transparent section; a light source, wherein the light source emits a beam; a light detector; a digital image data acquisition device; and, an image data processing unit; pairing the plurality of polymeric sheets with the plurality of chucks to provide a plurality of sheeted chucks; wherein each sheeted chuck in the plurality of sheeted chucks comprises an associated polymeric sheet held thereto by the holding region such that the impinging surface of the associated polymeric sheet is held substantial flat against the top surface; conveying the plurality of sheeted chucks, one at a time, between the light source and the light detector; wherein the beam emitted from the light source is oriented to pass through the central transparent section and impinge on the impinging surface; and, wherein the light detector is oriented to detect a transmitted light from the beam that is transmitted through the central transparent section and the thickness, $T_S$, and out the transmission surface; wherein the transmitted light has at least one detectable property; wherein the at least one detectable property includes an intensity of the transmitted light; wherein the intensity of the transmitted light is converted into an electrical signal by the light detector; wherein the electrical signal from the light detector is converted into a digital signal by the digital image data acquisition device; and, wherein the digital signal from the digital image data acquisition device is processed by the image data processing unit, wherein the image data processing unit is configured to detect macro inhomogeneities and to classify polymeric sheets as either acceptable or suspect; and, wherein the plurality of polymeric sheets is divided into a population of acceptable sheets and a population of suspect sheets.

Preferably, in the method of the present invention for analyzing polymeric sheets for use as polishing layers in chemical mechanical polishing pads, the polishing layer analyzer comprises a magazine designed to hold, store and dispense a plurality of sheeted chucks. Preferably, the magazine is designed to hold, store and dispense a plurality of sheeted chucks, wherein each sheeted chuck comprises a bound polymeric sheet held thereto by the holding region such that the impinging surface of the bound polymeric sheet is held substantially flat against the top surface. Preferably, the magazine has a design capacity for holding at least 10 sheeted chucks (more preferably, at least 15 sheeted chucks; still more preferably, at least 20 sheeted chucks; most preferably, at least 30 sheeted chucks). The magazine design capacity enables an operator to load a plurality of sheeted chucks into a polishing layer analyzer. Once the plurality of sheeted chucks is loaded into the magazine, the operator is able to then perform other tasks while the polishing layer analyzer classifies the plurality of polymeric sheets paired with the plurality of chucks as either acceptable or suspect.

Preferably, in the method of the present invention for analyzing polymeric sheets for use as polishing layers in chemical mechanical polishing pads, each chuck (200) in the plurality of chucks has a holding region (240), surrounding a peripheral edge (235) of a central transparent section (220); wherein the holding region (240) has a contacting surface (245), a plurality of concentric grooves (250), and a plurality of vacuum ports (260); wherein each concentric groove (250) has a pair of sidewalls (255) and a base (253). More preferably, each chuck (200) has a holding region (240), surrounding the peripheral edge (235) of the central transparent section (220); wherein the holding region (240) has a contacting surface (245), a plurality of concentric grooves (250), and a plurality of vacuum ports (260); wherein each concentric groove (250) has a pair of sidewalls (255) and a base (253); wherein each sidewall (255) is substantially perpendicular to the contacting surface (245).

Preferably, in the method of the present invention for analyzing polymeric sheets for use as polishing layers in chemical mechanical polishing pads, the polishing layer analyzer further comprises a sequencer; wherein the sequencer is configured to load and extract sheeted chucks from the magazine. Preferably, the sequencer is configured to load and extract sheeted chucks from the magazine one at a time. Preferably, the sequencer is further configured to convey sheeted chucks, one at a time, to a position interposed between a light source and a light detector; and, returning the sheeted chucks, one at a time, back into the magazine. Preferably, the sequencer includes at least one linear motor. More preferably, the sequencer includes at least one linear motor having a linear scale resolution of ≤1 µm.

Preferably, in the method of the present invention for analyzing polymeric sheets for use as polishing layers in chemical mechanical polishing pads, the polishing layer analyzer further comprises a sequencer, wherein the sequencer is configured to extract from the magazine and convey sheeted chucks, one at a time, to a position interposed between the light source and the light detector; wherein the beam emitted from the light source is oriented to pass through the central transparent section of the sheeted chuck and impinge on the impinging surface of the bound polymeric sheet; and, wherein the light detector is oriented to detect a transmitted light from the beam that is transmitted through the thickness, $T_S$, and out the transmission surface; wherein the light detector is configured to convert an intensity of the transmitted light into an electrical signal; wherein the digital image data acquisition device coupled to the light detector is configured to covert the electrical signal from the light detector into a digital signal; wherein the image data processing unit coupled to the digital image data acquisition device is configured to process the digital signal from the digital image data acquisition device to detect macro inhomogeneities and to classify polymeric sheets as either acceptable for use as a polishing layer in a chemical mechanical polishing pad, or as suspect; wherein the plurality of polymeric sheets is divided into a population of acceptable sheets and a population of suspect sheets.

Preferably, in the method of the present invention for analyzing polymeric sheets for use as polishing layers in chemical mechanical polishing pads, the light source emits a beam. Preferably, the beam emitted by the light source exhibits an emission spectrum including wavelengths selected from at least one of the visible, ultraviolet and infrared regions. Preferably, the light source is selected from a broad band source (e.g., a white light source) and a narrow band source (e.g., a narrow band blue light source). More preferably, the light source is a narrow band blue light source. Still more preferably, the light source is a narrow band blue light source that emits a beam, wherein the beam exhibits an emission spectrum having a peak wavelength of 460 to 490 nm (preferably, 460 to 480 nm; more preferably, 460 to 470; most preferably, 463 to 467 nm) and a full width at half maximum intensity, FWHM, of ≤50 nm (preferably, ≤40 nm; more preferably, ≤35 nm; most preferably, ≤30 nm). One or ordinary skill in the art will be able to select an appropriate light source for providing a beam with an emission spectrum in the desired region. Preferably, in the method of the present invention, the automated inspection system comprises a light source, wherein the light source is a light emitting diode.

Preferably, in the method of the present invention for analyzing polymeric sheets for use as polishing layers in chemical mechanical polishing pads, the light detector is capable of converting the at least one detectable property of the transmitted light from the beam that is transmitted through the thickness, $T_S$, and out the transmission surface of a polymeric sheet. More preferably, in the method of the present invention for analyzing polymeric sheets for use as polishing layers in chemical mechanical polishing pads, the light detector is capable of converting an intensity of the transmitted light from the beam that is transmitted through the thickness, $T_S$, and out the transmission surface of a polymeric sheet. Most preferably, in the method of the present invention for analyzing polymeric sheets for use as polishing layers in chemical mechanical polishing pads, the light detector capable of converting an intensity and a wavelength spectrum of the transmitted light from the beam that is transmitted through the thickness, $T_S$, and out the transmission surface of a polymeric sheet. Preferably, the light detector is an optoelectric converting device, which converts the at least one detectable property of the transmitted light incident thereon into an electric signal. Preferably, the light detector is an array of charge coupled devices (CCDs). Preferably, the charge coupled devices (CCDs) used are selected from monochromatic and color CCDs. More preferably, the light detector comprises an array of at least 5 (most preferably, at least 8) optoelectric converting devices. Most preferably, the light detector comprises an array of at least 8 charge coupled devices (CCD) image sensors having a resolution of ≤20 μm (preferably, ≤16 μm) and a field of view of ≥100 mm (preferably, ≥120 mm).

The digital image data acquisition device converts to a digital signal the electrical signal output from the light detector. Digital image data acquisition devices suitable for use with the present invention are well known in the art.

The heterogeneous compositional nature of polymeric sheets comprising a polymer microelement composite makes reference to a hypothetical standard sheet impractical. That is, the existence of various, innocuous production artifacts in such polymeric sheets make simple grayscale comparison to a standard value ineffective for use in an automated system for inspecting polymeric sheets for incorporation as a polishing layers in chemical mechanical polishing pads.

General purpose and specialty purpose image data processing units suitable for use with the present invention are well known in the art. Preferably, the image data processing unit in the automated inspection system used in the method of the present invention, comprises a central processing unit coupled to a non-volatile data storage unit.

Preferably, the central processing unit is further coupled to one or more user input interface controllers (e.g., mouse, keyboard) and at least one output display.

Preferably, image data processing unit is configured to detect macro inhomogeneities in the polymeric sheets and to classify the polymeric sheets as either acceptable or suspect. Preferably, the classification of the polymeric sheets as acceptable or suspect is performed by the image data processing unit based on a menu of quality control criteria. A variety of defects can occur during the manufacture of the polymeric sheets including, for example, density defects, air hole defects and inclusion defects. Note that any one or a combination of these defects can constitute a macro inhomogeneity in a polymeric sheet depending on the size of the affected portion of the transmission surface. Note that the various defect types will present differently to the light detector. For density defects and air holes, the defective region will be more transparent than the surrounding region of the polymeric sheet. For inclusion defects, the defective region will be less transparent than the surrounding region of the polymeric sheet. Whether such defects are acceptable depends on a number of conditions, including, for example, the substrate for which the chemical mechanical polishing pad incorporating the polymeric sheet will be tasked for polishing. Certain substrates are more delicate than others, and hence require tighter controls on the homogeneity of the polymeric sheets to be used as polishing layers in chemical mechanical polishing pads manufactured for their polishing.

Preferably, in the method of the present invention for analyzing polymeric sheets for use as polishing layers in chemical mechanical polishing pads, wherein the population of suspect sheets includes at least one suspect sheet and wherein the at least one suspect sheet contains at least one detected macro inhomogeneity; the image data processing unit is preferably further configured to produce and store in a nonvolatile memory a map of the at least one suspect sheet, wherein a location for the at least one detected macro inhomogeneity is positioned.

Preferably, in the method of the present invention for analyzing polymeric sheets for use as polishing layers in chemical mechanical polishing pads, wherein the population of suspect sheets includes at least one suspect sheet and wherein the at least one suspect sheet contains at least one detected macro inhomogeneity; the method, further comprises: choosing a select sheet from the population of suspect sheets; wherein the image data processing unit is preferably further configured to produce and store in a nonvolatile memory a map of the at least one suspect sheet, wherein a location for the at least one detected macro inhomogeneity is positioned.

Preferably, in the method of the present invention for analyzing polymeric sheets for use as polishing layers in chemical mechanical polishing pads, wherein the population of suspect sheets includes at least one suspect sheet and wherein the at least one suspect sheet contains at least one detected macro inhomogeneity; the method, further comprises: choosing a select sheet from the population of suspect sheets; wherein the image data processing unit is preferably further configured to produce and store in a nonvolatile memory a map of the at least one suspect sheet, wherein a location for the at least one detected macro inhomogeneity is positioned; and, wherein the polishing layer analyzer, further comprises: a display; wherein an image of the select sheet is displayed on the display. The image displayed of the select sheet on the display can be an image of the entirety of the transmission surface of the select sheet. Preferably, the image of the select sheet is a partial image showing a magnification of at least one detected macro inhomogeneity. Preferably, the partial image of the select sheet displayed on the display includes the entirety of the macro inhomogeneity and the surrounding region of the transmission surface of the select sheet. Preferably, the partial image of the select sheet displayed on the display can be magnified to enhance the detail of the displayed image to facilitate a visual inspection of the select sheet. Preferably, the method of the present invention, further comprises: performing a visual inspection of the select sheet, wherein the visual inspection is facilitated by the image of the select sheet displayed on the display; and, either (i) reclassifying the select sheet, based on the visual inspection, as acceptable, wherein the select sheet is then added to the population of acceptable sheets; or, (ii) classifying the select sheet, based on the visual inspection, as defective, wherein the select sheet is then added to a population of defective sheets.

Figure 7:
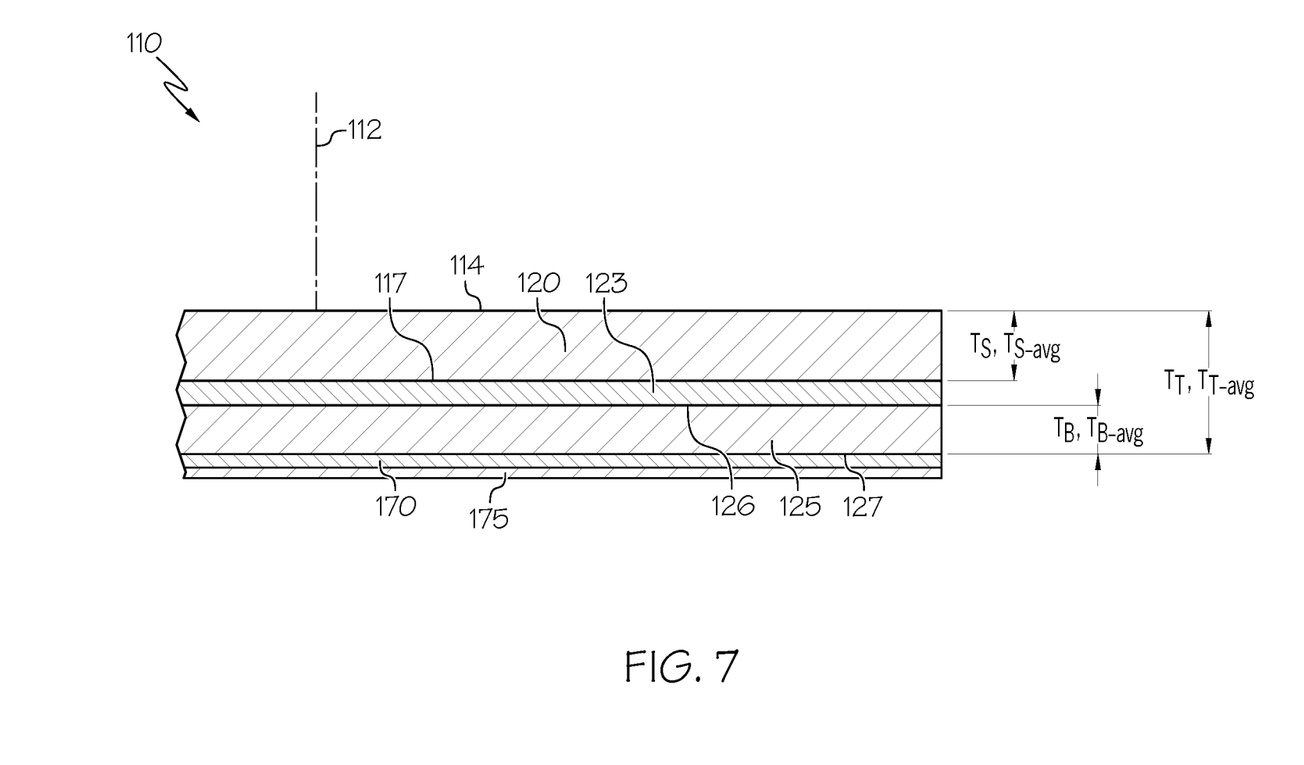
FIG. 7 is a depiction of a cross sectional cut away view of a chemical mechanical polishing pad incorporating, as a polishing layer, a polymeric sheet.

Preferably, the method of the present invention for analyzing polymeric sheets for use as polishing layers in chemical mechanical polishing pads, further comprises: processing at least one acceptable sheet to form a polishing layer (120) of a chemical mechanical polishing pad (110); wherein the polishing layer (120) is adapted for polishing a substrate; wherein the processing comprises: forming a polishing surface (114) by at least one of (a) machining at least one groove into the acceptable sheet to form a polishing groove pattern and (b) forming perforations that extend at least part way through the thickness, $T_s$, of the acceptable sheet. More preferably, the method further comprises: processing at least one acceptable sheet to form a polishing layer (120) of a chemical mechanical polishing pad (110); wherein the polishing layer (120) is adapted for polishing a substrate; wherein the processing comprises forming a polishing surface (114) by machining at least one polishing groove into the acceptable sheet to form a polishing groove pattern. Most preferably, the method further comprises: processing at least one acceptable sheet to form a polishing layer (120) of a chemical mechanical polishing pad (110);

wherein the polishing layer (120) is adapted for polishing a substrate; wherein the processing comprises forming a polishing surface (114) by machining at least one polishing groove into the acceptable sheet to form a polishing groove pattern; wherein the polishing groove pattern is adapted for polishing the substrate. (See FIG. 7).

Preferably, the method of the present invention provides chemical mechanical polishing pads (110) preferably adapted for rotation about a central axis (112). (See FIG. 7). Preferably, the at least one polishing groove is arranged to form a polishing surface (114) such that upon rotation of the pad (110) about the central axis (112) during polishing, at least one polishing groove sweeps over the substrate. Preferably, the at least one polishing groove is selected from curved polishing grooves, linear polishing grooves and combinations thereof. Preferably, the at least one polishing groove has a depth of ≥10 mils (preferably, 10 to 150 mils). Preferably, the at least one polishing groove forms a polishing groove pattern that comprises at least two polishing grooves having a combination of a depth selected from ≥10 mils, ≥15 mils and 15 to 150 mils; a width selected from ≥10 mils and 10 to 100 mils; and a pitch selected from ≥30 mils, ≥50 mils, 50 to 200 mils, 70 to 200 mils, and 90 to 200 mils.

Preferably, the polymeric sheet incorporated as polishing layer (120) into the chemical mechanical polishing pad (110) contains <1 ppm abrasive particles incorporated therein.

Preferably, in the method of the present invention, processing the at least one acceptable sheet, further comprises: providing a subpad (125) having a top surface (126) and a bottom surface (127); providing an adhesive (123)(preferably, wherein the adhesive is selected from at least one of a pressure sensitive adhesive, a hot melt adhesive and a contact adhesive; more preferably wherein the adhesive is selected from a pressure sensitive adhesive and a hot melt adhesive; most preferably, wherein the adhesive is a hot melt adhesive); and, laminating the top surface (126) of the subpad (125) to the base surface (117) of the polishing layer (120) using the adhesive (123). (See FIG. 7).

Preferably, in the method of the present invention, processing the at least one acceptable sheet to form the polishing layer (120) of the chemical mechanical polishing pad (110); wherein the polishing layer (120) is adapted for polishing a substrate, further comprises: providing a pressure sensitive platen adhesive layer (170) applied to the bottom surface (127) of the subpad (125).

Preferably, in the method of the present invention, processing the at least one acceptable sheet to form the polishing layer (120) of the chemical mechanical polishing pad (110); wherein the polishing layer (120) is adapted for polishing a substrate, further comprises: providing a pressure sensitive platen adhesive layer (170) applied to the bottom surface (127) of the subpad (125); and, providing a release liner (175) applied over the pressure sensitive platen adhesive layer (170), wherein the pressure sensitive platen adhesive layer (170) is interposed between the bottom surface (127) of the subpad (125) and the release liner (175). (See FIG. 7).

The incorporation of a subpad (125) into a chemical mechanical polishing pad (110) of the present invention is desirable for certain polishing applications. One of ordinary skill in the art will know to select an appropriate material of construction and subpad thickness, $T_B$, for the subpad (125) for use in the intended polishing process. Preferably, the subpad (150) has an average subpad thickness, $T_{B-avg}$, of ≥15 mils (more preferably, 30 to 100 mils; most preferably 30 to 75 mils).

Preferably the adhesive (123) is selected from the group consisting of a pressure sensitive adhesive, a reactive hot melt adhesive, a contact adhesive and combinations thereof. More preferably, the adhesive (123) is selected from the group consisting of a pressure sensitive adhesive and a reactive hot melt adhesive. Most preferably, the adhesive (123) is a reactive hot melt adhesive.

Preferably, in the method of the present invention, processing the at least one acceptable sheet to form the polishing layer (120) of the chemical mechanical polishing pad (110); wherein the polishing layer (120) is adapted for polishing a substrate, further comprises: providing at least one additional layer (not shown) interfaced with and interposed between the polishing layer (120) and the pressure sensitive platen adhesive layer (170). The at least one additional layer (not shown) can be incorporated into the chemical mechanical polishing pad (110) using an additional layer adhesive (not shown). The additional layer adhesive can be selected from pressure sensitive adhesives, hot melt adhesives, contact adhesives and combinations thereof. Preferably, the additional layer adhesive is a hot melt adhesive or a pressure sensitive adhesive. More preferably, the additional layer adhesive is a hot melt adhesive.

Preferably, the method of the present invention provides chemical mechanical polishing pads (110) specifically designed to facilitate the polishing of a substrate selected from at least one of a magnetic substrate, an optical substrate and a semiconductor substrate. Preferably, the polymeric sheets are adapted for polishing a substrate selected from at least one of a magnetic substrate, an optical substrate and a semiconductor substrate (more preferably, a semiconductor substrate; most preferably, a semiconductor wafer).

We claim:

1. A polishing layer analyzer for analyzing polymeric sheets for use as polishing layers in chemical mechanical polishing pads, the polishing layer analyzer comprising:
   a magazine; and,
   a plurality of chucks, wherein each chuck in the plurality of chucks:
   (a) comprises:
      a central transparent section with a top surface, a bottom surface and a peripheral edge; wherein the top surface is substantially parallel with the bottom surface; and, wherein the top surface is substantially smooth; and,
      a holding region, surrounding the peripheral edge of the central transparent section; wherein the holding region comprises a contacting surface, a plurality of concentric grooves, and a plurality of vacuum ports; wherein the plurality of vacuum ports are in communication with the plurality of concentric grooves to facilitate applying of a vacuum to the plurality of concentric grooves; wherein the contacting surface is substantially planar with the top surface of the central transparent section; wherein the plurality of concentric grooves have a groove width, W, and a groove pitch, P; and, wherein W<P; and,
   (b) is configured to hold a polymeric sheet substantially flat against the top surface of the central transparent section; wherein the polymeric sheet (i) comprises: a polymer microelement composite, comprising: a polymer and a plurality of microelements, wherein the plurality of microelements are dispersed in the polymer; and, (ii) has a transmission surface, an impinging surface and a thickness, $T_S$, between the transmission surface and the impinging surface;

wherein the transmission surface and the impinging surface are substantially parallel;

wherein the magazine has a capacity for storing the plurality of chucks; and, wherein the magazine is designed to load, store and dispense the plurality of chucks to facilitate an analysis of a plurality of polymeric sheets.

2. The polishing layer analyzer of claim 1, further comprising:

a sequencer;

a light source, wherein the light source emits a beam;

a light detector;

a digital image data acquisition device coupled to the light detector; and, an image data processing unit coupled to the digital image data acquisition device;

wherein the sequencer is configured to extract from the magazine and convey the plurality of chucks, one at a time, to a position interposed between the light source and the light detector; wherein the beam emitted from the light source is oriented to pass through the central transparent section and impinge on the impinging surface; and, wherein the light detector is oriented to detect a transmitted light from the beam that is transmitted through the central transparent section and the thickness, $T_S$, and out the transmission surface; wherein the light detector is configured to convert an intensity of the transmitted light into an electrical signal; wherein the digital image data acquisition device coupled to the light detector is configured to covert the electrical signal from the light detector into a digital signal; wherein the image data processing unit coupled to the digital image data acquisition device is configured to process the digital signal from the digital image data acquisition device to detect macro inhomogeneities and to classify polymeric sheets as either acceptable for use as a polishing layer in a chemical mechanical polishing pad, or as suspect; wherein the plurality of polymeric sheets is divided into a population of acceptable sheets and a population of suspect sheets.

3. The polishing layer analyzer of claim 2, wherein the sequencer is further configured to return the plurality of chucks to the magazine.

4. The polishing layer analyzer of claim 3, wherein the plurality of chucks includes at least 10 chucks.

5. The polishing layer analyzer of claim 2, further comprising:

a display to facilitate visual inspection of the plurality of polymeric sheets.

* * * * *